(12) United States Patent
Von Der Haar

(10) Patent No.: US 6,535,571 B2
(45) Date of Patent: Mar. 18, 2003

(54) DETECTOR FOR AN X-RAY COMPUTED TOMOGRAPHY APPARATUS

(75) Inventor: Thomas Von Der Haar, Nuernberg (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/813,436

(22) Filed: Mar. 20, 2001

(65) Prior Publication Data

US 2001/0050970 A1 Dec. 13, 2001

(30) Foreign Application Priority Data

Mar. 27, 2000 (DE) .......................... 100 15 191
Oct. 24, 2000 (DE) .......................... 100 52 827

(51) Int. Cl.⁷ .............................. H05G 1/60
(52) U.S. Cl. ..................... 378/19; 250/370.09
(58) Field of Search ................ 378/4, 19, 98.8; 250/370.09

(56) References Cited

U.S. PATENT DOCUMENTS 5,166,961 A * 11/1992 Brunnett et al. ............. 378/19
6,157,696 A * 12/2000 Saito et al. ................. 378/19
6,188,745 B1   2/2001 Gordon ..................... 378/19
6,215,843 B1 * 4/2001 Saito et al. ................. 378/19
6,243,438 B1 * 6/2001 Nahaliel et al. ............. 378/19
6,259,766 B1 * 7/2001 Cuppen .................... 378/147
6,400,793 B2 * 6/2002 Doubrava et al. ........... 378/19

FOREIGN PATENT DOCUMENTS

DE        195 02 574        8/1996
WO        WO 98/05980       2/1998

* cited by examiner

Primary Examiner—Drew A. Dunn
Assistant Examiner—Allen C Ho
(74) Attorney, Agent, or Firm—Schiff Hardin & Waite

(57) ABSTRACT

A detector for an X-ray computed tomography apparatus has a number of detector elements b1 . . . b10 separated from one another by septa. In order to fashion the detector especially universally, the widths of the detector elements are selected such that a channel occupancy combination from the following group can be realized: [20×b1 or 20×b2 or 16×b4], [16×b1 or 16×b2 or 12×b4], [8×b1 or 8×b2 or 8×b4 or 8×b6], [4×b1 or 4×b2 or 4×b4 or 4×b8 or 4×b12], [8×b1 or 8×b2 or 8×b5], [4×b1 or 4×b2, 4×b4 or 4×b10].

5 Claims, 2 Drawing Sheets

DETECTOR FOR AN X-RAY COMPUTED TOMOGRAPHY APPARATUS

BACKGROUND OF THE INVENTION

1. Field of the Invention

The present invention is directed to a detector for an X-ray computed tomography apparatus of the type having a number of detector elements of different widths separated from one another by septa, forming a detector line arranged in a direction of a rotational axis of the tomography apparatus, with a number of such detector lines being arranged next to each other, and wherein a predetermined number of channels are provided for acquiring signals generated by the detector elements, with one or more of the detector elements being selectively connectable to respective ones of the channels for acquiring the signals.

2. Description of the Prior Art

Detectors of the above general type are disclosed in German OS 195 02 574 and PCT Application WO 98/05980. They have a number of parallel detector lines that proceed in the direction of the axis of a subject to be transirradiated, for example a patient. Each detector line is composed of a number of detector elements that, for example, are manufactured of a scintillator ceramic.

For readout of the signals generated by the detector elements, usually four, currently at most eight, channels are available dependent on the computing power of the computer. Dependent on the demands regarding the desired image information, a number of detector elements lying next to one another in a detector line can be respectively connected to one channel. When, for example, two or more detector elements of a detector line are connected to one channel, information about a relatively large volume excerpt of the transirradiated subject is obtained. Such an information is especially well-suited for producing high-contrast images with which, for example, it is possible to differentiate soft parts in the brain.

When, in contrast, only one detector element from each line is respectively connected to each of the channels, the transirradiated volume is small. The information thus obtained is especially well-suited for the resolution of fine structures, for example in the inner ear region.

For gating the required, fan-shaped X-ray beam, a diaphragm precedes the known detector. The provision of such a diaphragm causes increased manufacturing outlay. Moreover, the detector has a number of detector elements with a number of septa separating them. The efficiency of such a detector is not especially high. The multitude of provided detector elements further increases the manufacturing outlay of the detector.

SUMMARY OF THE INVENTION

An object of the invention is provide a simply constructed, universal detector with enhanced efficiency for an X-ray computed tomography apparatus.

This object is achieved in accordance with the invention in a detector of the type initially described wherein the widths of the detector elements are selected such that a channel occupancy combination selected from the following group can be realized: [20×b1 or 20×b2 or 16×b4], [16×b1 or 16×b2 or 12×b4], [8×b1 or 8×b2 or 8×b4 or 8×b6], [4×b1 or 4×b2 or 4×b4 or 4×b8 or 4×b12], [8×b1 or 8×b2 or 8×b5], [4×b1 or 4×b2, 4×b4 or 4×b10], wherein the detector elements are designated b1 ... b10.

In terms in the above, such as 20×b1 or 12×b4, for example, b1 designates a slice having a thickness equal 1 times the thickness of a detector element referenced b1, and b4 designates a slice having a thickness equal to 4 times the thickness of the detector element referenced b1. Slice combination 20×b1 can be scanned if 20 electronics channels are available, while 12 electronics channels are sufficient to stand the slice combination 12×b4.

A detector that enables the inventive channel combination can have a minimized number of septa with respect to the selected channel occupancy combination. The efficiency, particularly the quantum efficiency, of such a detector is enhanced. A diaphragm preceding the detector can be foregone. This, in particular, reduces the cost outlay for the manufacture of the X-ray computer tomograph.

Expediently, the septa are symmetrically arranged with reference to a symmetry plane of the detector line that proceeds perpendicular to the rotational axis. This further facilitates manufacture.

The detector elements have respective widths B1 ... B10. A smallest, first width B1 can have a value selected from the following group: 0.375 mm, 0.5 mm, 0.625 mm, 0.75 mm, 1.0 mm. A tenth width B10 can amount to ten times, an eighth width B8 to eight times, a sixth width B6 to six times, a fifth width B5 to five times, a fourth width B4 to four times and a second width B2 to twice the first width B1. According to a further feature, the overall width of the detector line is 40 times, 48 times or 64 times the first width B1.

DESCRIPTION OF THE PREFERRED EMBODIMENTS

Figure 1:
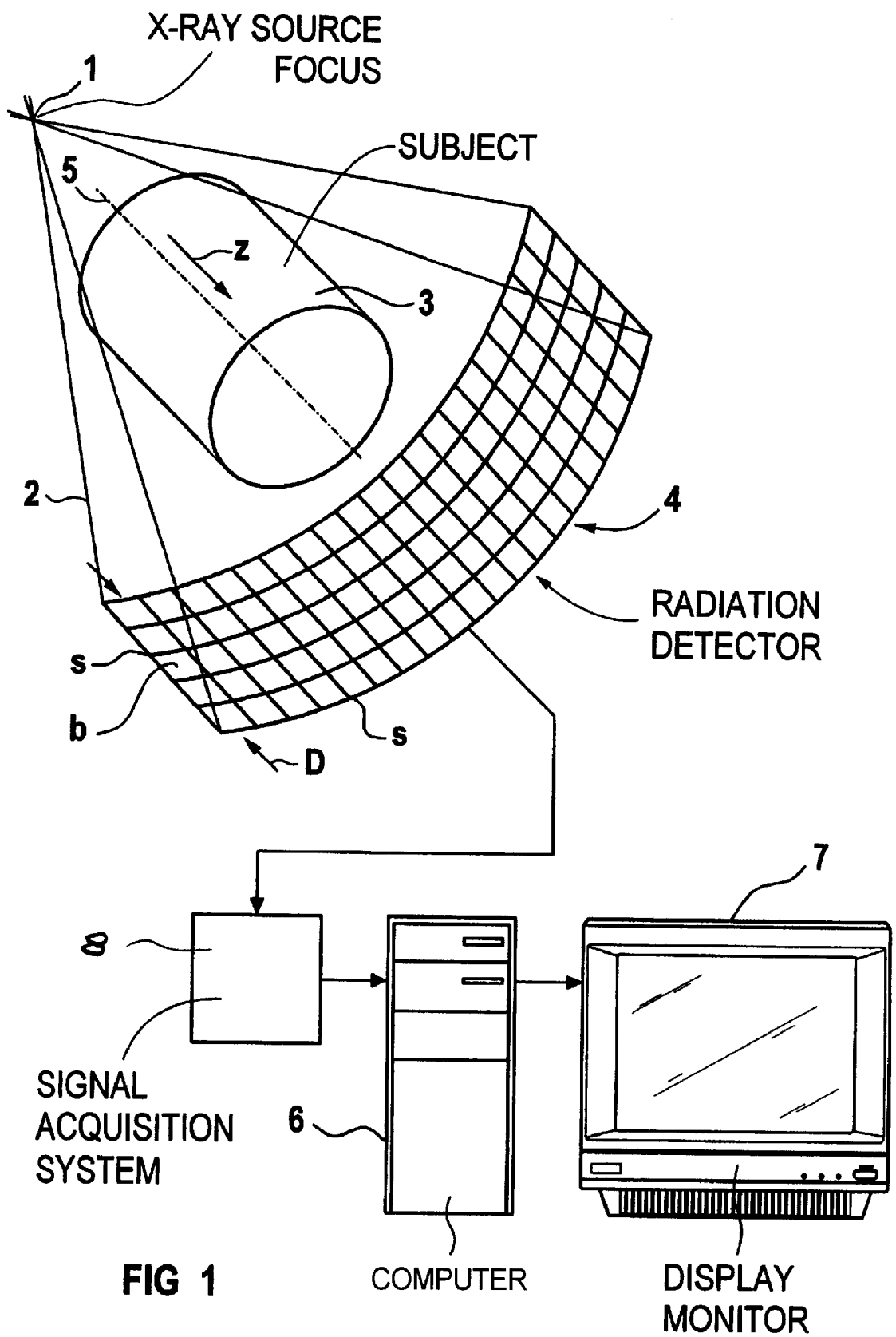
FIG. 1 shows the schematic structure of a known X-ray computed tomography apparatus.

FIG. 1 shows a focus 1 of an X-ray source from which a fan-shaped X-ray beam 2 gated by a diaphragm (not shown) emanates. The beam 2 penetrates a subject 3 and strikes a detector 4. The detector 4 is formed by a number of parallel detector lines D, each thereof being formed by a row of detector elements b. The detector elements b are respectively separated from one another by septa s.

The measuring system 1, 4 is rotatable around a rotational axis 5, so that the subject 3 is transirradiated from different projections during which the detector lines D are read out by a signed acquisition system 8. A computer 6 calculates an image of the subject 3 from the detector signals that are thereby formed, said image being reproduced on a monitor 7.

In FIGS. 2 through 8, examples of detector lines D in accordance with the invention, formed of a number of detector elements b that are in turn separated from one another by septa s, are shown. Each of the detector elements b, for example, is manufactured of a scintillator ceramic facing toward the incident X-radiation that is connected to a light sensitive resistor (not shown here) at its side facing away from the radiation entry side. The light-sensitive resistor can in turn be optionally connected to one or more available electronics channels.

Figure 2:
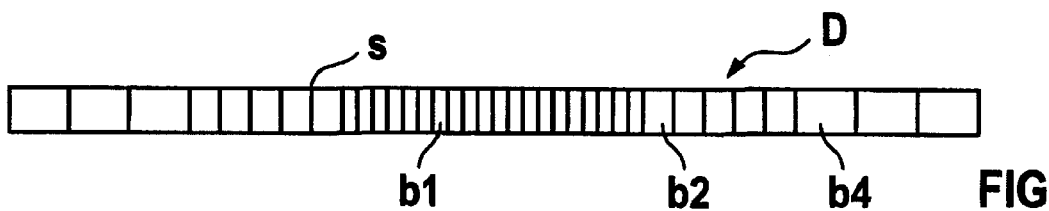
FIG. 2 is a schematic illustration of a first detector line in accordance with the invention.

Given the first detector line D shown in FIG. 2, twenty first detector elements b1 each having a first width B1 are provided in a symmetrical arrangement, B1 being the minimum width. The first width B1 can, for example, amount to 0.375 mm, 0.5 mm, 0.625 mm, 0.75 mm or 1.0 mm. Five second detector elements b2 with the width B2 respectively adjoin in a symmetrical arrangement at both sides of the first detector elements b1. The width B2 is twice as wide as the width B1. Three fourth detector elements b4 adjoin at each of the sides of the detector elements b2, the fourth width B4 thereof corresponding to four times the first width B1. The proposed structuring has 64 times the first width B1. In particular, the following slice combinations thus can be activated: 20×b1, 20×b2, 16×b4.

Figure 3:
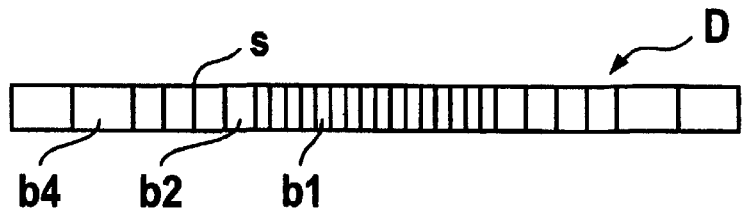
FIG. 3 is a schematic illustration of a second detector line in accordance with the invention.

Given the detector line D shown in FIG. 3, four second detector elements b2 at each side adjoin sixteen first detector elements b1, and two fourth detector elements b4 adjoin each of the groups of second detector elements b2. The arrangement is symmetrical. The overall length of this detector line D amounts to 48 times the first width B1. The following slice combinations can be activated on, for example, the 16 electronics channels that are available: 20×b1, 20×b2, 12×b4.

Figure 4:
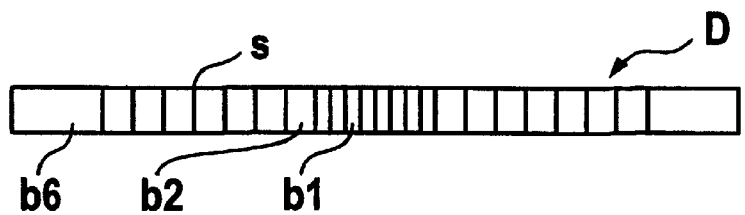
FIG. 4 is a schematic illustration of a third detector line in accordance with the invention.

Given the third detector line D shown in FIG. 4, seven second detector elements b2 at each side adjoin eight centrally disposed first detector elements b1, and a sixth detector element b6 adjoins each of the groups of second detector elements b2. The sixth detector element b6 exhibits six times the width of the first width B1. The overall length of this detector line D again amounts to 48 times the first width B1. The following slice combinations can be activated on, for example, the eight electronics channels that are available: 8×b1, 8×b2, 8×b4, 8×b6.

Figure 5:
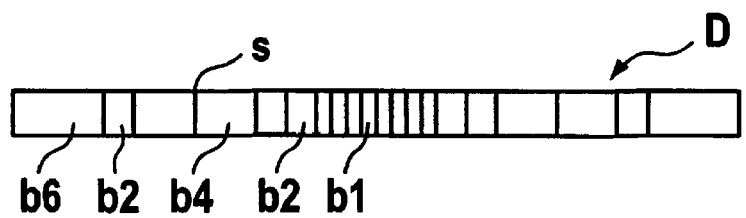
FIG. 5 is a schematic illustration of a fourth detector line in accordance with the invention.

Given the fourth detector line D shown in FIG. 5, two second detector elements b2 at each side adjoin eight centrally disposed first detector elements b1, two fourth detector elements b4 in turn adjoin the groups of second detector elements b2 at each side, a second detector element b2 in turn following thereupon at each side and a sixth detector element b6 in turn following thereupon at each side. In this embodiment, the width B of the detector elements b does not increase steadily toward ends the of the detector line. The overall length of this detector line D amounts to 48 times the first width B1. The following slice combinations can thus be activated on, for example, the eight electronics channels that are available: 8×b1, 8×b2, 8×b4, 8×b6.

Figure 6:
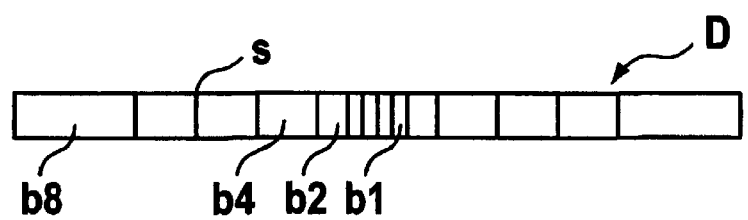
FIG. 6 is a schematic illustration of a fifth detector line in accordance with the invention.

Given the fifth detector line D shown in FIG. 6, one second detector element b2 at each side adjoins four first detector elements b1, three fourth detector elements b4 adjoin each second detector element b2, and an eighth detector element b8 following thereupon at each side. An eighth width of the eighth detector element b8 amounts to eight times the first width B1. The overall length of this detector line D amounts to 48 times the width of the detector element b1. The following slice combinations can thus be activated on, for example, the four electronics channels that are available: 4×b1, 4×b2, 4×b4, 4×b8, 4×b12 .

The slice combination 4×b12 set forth above means that one can combine a total of two detector elements b8, six detector elements b4, two detector elements b2, four detector elements b1, from left to right in the figure, with one of four electronics channels respectively, as follows:

1. One detector element b8 and one detector element b4 to a slice having 12 times the thickness of a detector element referenced b1;
2. Two detector elements b4, one detector element b2 and two detector elements b1 to a slice having 12 times the thickness of a detector element referenced b1;
3. Two detector elements b1, one detector element b2 and two detector elements b2 to a slice having 12 times the thickness of a detector element referenced b1; and/or
4. One detector element b4 and one detector element b8 to a slice having 12 times the thickness of a detector element referenced b1.

This results in a slice combination of 4×b12 which can be scanned with 4 electronics channels without the necessity of actually having detector elements of a width equal to 12 times the width of a detector element referenced b1.

Figure 7:
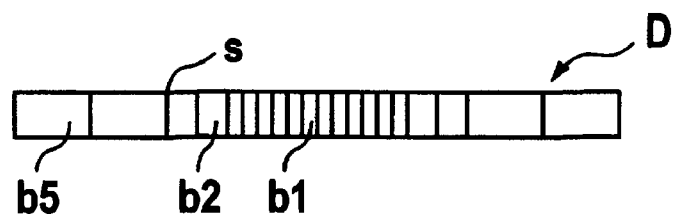
FIG. 7 is a schematic illustration of a sixth detector line in accordance with the invention.

Given the sixth detector line D shown in FIG. 7, two second detector elements b2 at each side adjoins twelve first detector elements b1, and two fifth detector elements b5 in turn adjoin the second detector elements b2 at each side. The overall length of this detector line D corresponds to 40 times the first width B1. The following slice combinations can thus be activated on, for example, the eight electronics channels that are available: 8×b1, 8×b2, 8×b5.

Figure 8:
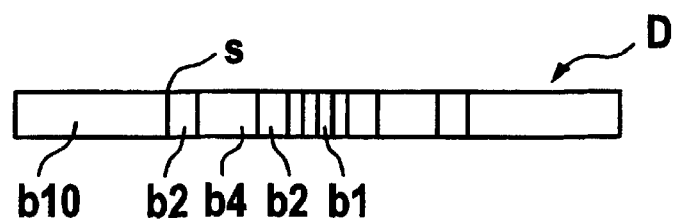
FIG. 8 is a schematic illustration of a seventh detector line in accordance with the invention.

Given the seventh detector line D shown in FIG. 8, one second detector element b2 at each side adjoins four first detector elements b1, a fourth detector element b4 follows thereupon at each side, a second detector element b2 follows thereupon at each side, and a tenth detector element b10 follows thereupon at each side. A tenth width B10 of the tenth detector element b10 amounts to ten times the first width B1. The overall length of this detector line D again amounts to 40 times the first width B1. The following slice combinations can thus be activated on, for example, the four electronics channels that are available: 4×b1, 4×b2, 4×b4, and 4×b10.

All of the inventive detector lines D are symmetrical relative to a symmetry plane proceeding parallel to the z-axis. The structures of the detector lines D enable a minimization of the septa s, and thus an increase in the quantum efficiency. Detector arrays for X-ray computed tomography systems to be universally operated can be manufactured with the inventive detector lines D. Such X-ray computed tomography systems do not require the provision of a diaphragm inserted into the beam path.

Although modifications and changes may be suggested by those skilled in the art, it is the intention of the inventor to embody within the patent warranted hereon all changes and modifications as reasonably and properly come within the scope of his contribution to the art.

I claim as my invention:

1. A detector for an X-ray computed tomography apparatus comprising a plurality of detector elements b1 . . . b10 of respectively different widths B1 . . . B10 separated from one another by septa forming a detector line arranged in a direction of a rotational axis of the tomography apparatus, with a plurality of detector lines arranged next to one another, a predetermined plurality of channels for acquiring signals generated by the detector elements b1 . . . b10, with one or more of the detector elements b1 . . . b10 being selectively connectable to respective ones of the channels for acquiring the signals, the widths of the detector elements being selected such that a channel occupancy combination selected from the group consisting of [20×b1 or 20×b2 or 16×b4], [16×b1 or 16×b2 or 12×b4], [8×b1 or 8×b2 or 8×b4 or 8×b6], [4×b1 or 4×b2 or 4×b4 or 4×b8 or 4×b2], [8×b1 or 8×b2 or 8×b5] and [4×b1 or 4×b2 or 4×b4 or 4×b10] can be realized.

2. A detector as claimed in claim 1, wherein the septa are symmetrically arranged with respect to a symmetry plane of the detector line that proceeds perpendicular to the rotational axis.

3. A detector as claimed in claim 1, wherein a smallest, first width B1 has a value selected from the group consisting of 0.375 mm, 0.5 mm, 0.625 mm, 0.75 mm, 1.0 mm.

4. A detector as claimed in claim 1, wherein a tenth width B10 amounts to ten times a first width B1, an eighth width B8 amounts to eight times the first width B1, a sixth width B6 amounts to six times the first width B1, a fifth width B5 amounts to five times the first width B1, a fourth width B4 amounts to four times the first width B1, and a second width B2 amounts to twice the first width B1.

5. A detector as claimed in claim 1, wherein an overall width of the detector line is a multiple selected from the group consisting of 40 times, 48 times, 64 times a first width B1.

* * * * *